United States Patent [19]

Donawick et al.

[11] Patent Number: 4,699,613
[45] Date of Patent: Oct. 13, 1987

[54] APPARATUS FOR THE GRAVITATIONAL ADMINISTRATION OF FLUIDS AND DRUGS TO LARGE ANIMALS

[76] Inventors: William J. Donawick, 1501 Brandywine Dr., West Chester, Pa. 19382; Betty L. Teichman, No. 4 Forest Hills, Poorhouse Rd., Downingtown, Pa. 19335

[21] Appl. No.: 812,159

[22] Filed: Dec. 23, 1985

[51] Int. Cl.$^4$ .............................................. A61M 5/00
[52] U.S. Cl. ..................................... 604/80; 604/257; 248/95
[58] Field of Search ................... 604/80, 81, 179, 257, 604/258, 259; 248/95, 341, 332, 339, 328

[56] References Cited

U.S. PATENT DOCUMENTS

| | | |
|---|---|---|
| Re. 16,251 | 1/1926 | Schellberg . |
| 2,669,231 | 2/1954 | Fischer .......................... 604/179 X |
| 2,954,028 | 9/1960 | Smith .................................... 128/214 |
| 3,177,870 | 4/1965 | Salem, Jr. et al. ..................... 604/81 |
| 3,756,237 | 9/1973 | Chittenden et al. .................. 604/80 |
| 3,924,781 | 12/1975 | Witte ................................. 248/95 X |
| 3,939,832 | 2/1976 | Miller ............................. 604/251 X |
| 4,034,754 | 7/1977 | Virag ..................................... 604/81 |
| 4,333,455 | 6/1982 | Bodicky .......................... 128/214.4 |
| 4,573,974 | 3/1986 | Ruschke .............................. 604/81 |
| 4,576,592 | 3/1986 | Danby ................................. 604/80 |

FOREIGN PATENT DOCUMENTS 160667 3/1921 United Kingdom .

*Primary Examiner*—Stephen C. Pellegrino
*Attorney, Agent, or Firm*—Seidel, Gonda, Goldhammer & Abbott

[57] ABSTRACT

A gravitational fluid administration apparatus for large animals includes: a mechanism to allow a person of average strength to lift, lower, and suspend containers of blood, plasma, parenteral fluids, drugs, and supplemental salt solutions weighing as much as 25 kg without injuring the animal or human personnel; a hanger to hold the fluid containers; and a swivel mechanism to allow the suspended fluid containers to turn as the animal moves and to prevent kinking of the associated tubing. Further, there are "primary" and "secondary" tubing systems. The purpose of the primary tubing system is to convey fluids and drugs from fluid containers to the animal through a closed system. The primary tubing system is composed of connectors, securing straps, Y connectors, a drip chamber, shut-off clamps, side ports for the infusion of drugs or supplemental fluids, and sampling blood, and a coil of tubing to permit lengthening or shortening the effective length of the system as the animal moves away from or approaches the suspended fluid containers. The purpose of the secondary tubing system is to interconnect the fluid containers. The secondary tubing system consists of connectors, tubing and a shut-off clamp.

8 Claims, 4 Drawing Figures

APPARATUS FOR THE GRAVITATIONAL ADMINISTRATION OF FLUIDS AND DRUGS TO LARGE ANIMALS

BACKGROUND OF THE INVENTION

1. Field Of The Invention

This invention relates to an apparatus for the gravitational administration of fluids and drugs to large animals.

2. Description Of The Prior Art

It is often necessary and appropriate to administer blood, plasma, drugs, electrolyte, and supplemental salt solutions intravenously to large animals (usually sheep, goats, swine, cattle, horses and etc., but the list may include other large exotic animals, e.g. deer, lions, llamas, tigers and etc.). It is possible to confine these animals within a reasonably small space, e.g. a stall or pen up to 14 foot square. But, it is sometimes difficult or impossible to tether them to fluid administrating devices without potentially injuring the animal, especially if they are in pain or frightened. In larger adult animals (weighing 500 to 1000 kg or more), it may be necessary to intravenously administer up to 20 liters per hour.

Presently, there is no safe, reliable system for rapid gravitational administration of blood, plasma, drugs, electrolyte, and supplemental salt solutions to large animals.

The problems which are encountered when attempting to administer the needed fluids to the animals are bacterial contamination of the fluids before and during administration, less than adequate rate of fluid flow, difficulty in hoisting and lowering the fluid containers to allow for gravitational flow, twisting of the tubing during administration which stop or limit flow, tangling of the tubing around the animal, and the inability to administer drugs and supplemental salt solutions simultaneously or obtain blood samples without opening the system to bacterial contamination.

Heretofore, fluid administration systems for animals have employed available disposable intravenous fluid administration sets designed for human beings. These sets provide the needed tubing, Y-connectors, flow control device and drip chamber. But, they do not achieve the required rate of flow, because of their small internal lumen diameter. Also, they do not provide the needed extension and retraction of functional tubing length to prevent the animal from becoming entangled in the apparatus as the animal moves about the stall. Further, the common fluid container is held in a fixed position above the animal and as the animal moves the tubing from the containers invariably becomes twisted, thus obstructing fluid flow. In addition, these systems designed for humans lack any mechanism to secure the tubing to the fluid containers and the animal, so they often become disconnected with loss of the fluid and the potential introduction of bacteria or air into the vein being used for fluid administration.

Sterile pyrogen free water and electrolyte solutions packaged in one, three and five liter closed, collapsible, FDA approved plastic bags with "universal" connectors are presently available from many medical supply houses. Further, there are 500 ml, one and three liter sterile empty plastic bags which can be filled with blood, plasma, supplemental salt solutions, sugar solutions, to name but a few examples, which could be hung from the hanger and connected to the tubing apparatus of the present invention.

PRIOR ART

U.S. Pat. No. Re. 16,251 discloses a medical apparatus for use in proctotherapy. The apparatus includes a pulley system for suspending fluid containers and Y-connectors for joining together a number of containers. U.S. Pat. No. Re. 16,251 does not suggest the use of swivels nor coiled tubing nor that animals may benefit for the use of the apparatus.

U.S. Pat. No. 2,954,028 discloses an apparatus for administering parenteral fluids to humans. The apparatus includes a plurality of suspended fluid containers linked together through a manifold. The fluids may be mixed in the manifold and then introduced into the patient. There is no suggestion that this apparatus should include a swivel or that it can be used on animals.

U.S. Pat. No. 4,333,455 discloses an injectable catheter device. The device includes a length of coiled tubing. This patent suggests that the coiled tubing is used to prevent a long catheter from contacting and sticking to itself as it is introduced into the human. This patent does not suggest that the coiled tubing can be used to provide an adjustable length of tubing which allows an animal to move about while receiving fluids or drugs. Nor does this patent suggest the problem solved by the present invention, namely an apparatus for the gravitational administration of fluids and drugs to large animals.

OBJECTS OF THE INVENTION

Accordingly, it is the object of the present invention to provide a reliable, safe method for the rapid, gravitational, and continuous intravenous administration of blood, plasma, drugs, electrolyte and supplemental salt solutions to large animals.

A further object of the present invention is to provide a closed, system to convey fluids from a sterile container to a vein of the animal to minimize the introduction of infection.

More particularly, it is the object of this invention to enable the large animal to be able to move about its stall, tethered, or confined while still receiving intravenous fluids by gravity.

Additionally the hanger offers the ability to hang two or more containers higher than the others so they empty first (while lower bags are still approximately onehalf full) providing a reservoir to maintain continuous flow while replacing the higher containers.

Additional objects and advantages will become apparent and a more thorough and comprehensive understanding may be had from the following description taken in conjunction with the accompanying drawings forming a part of its specification.

SUMMARY OF THE INVENTION

The present invention provides an apparatus for the gravitational administration of fluids and drugs from containers to an animal. The apparatus includes means for hanging a plurality of containers, means for vertically moving and suspending the hanger means, means for swivelling the hanger means wherein the swivel means is connected between the hanger means and the means for vertically moving and suspending, means for removably connecting the containers to the animal, means for securing the connecting means to the animal, the animal securing means being adjustably and moveably secured to the connecting means, and means for tying the connecting means to the container.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
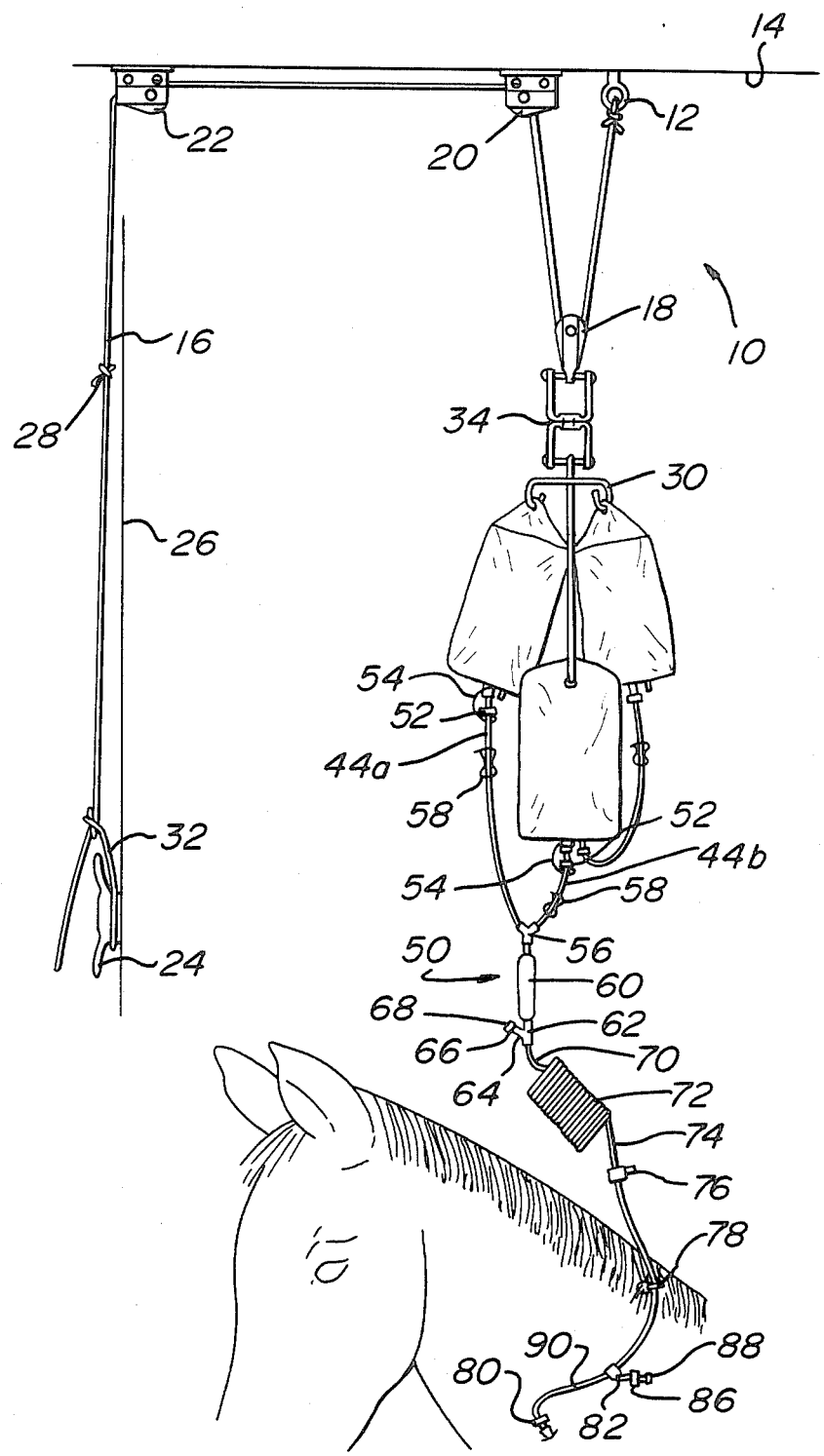
FIG. 1 is an elevational illustration of an apparatus made according to this invention which is installed within a stall and connected to a large animal and fluid container.

Referring now to FIG. 1, a typical installation of the pulley mechanism 10 to hoist, lower and suspend a hanger 30 for supporting fluid containers 10, is shown. An eye-ring 12 is placed as near as possible, to the center of a ceiling 14 of a stall. Of course, it will be understood by those skilled in the art that the placement of the apparatus herein described can be used at sites other than a stall, so long as the pulley mechanism is positioned overhead the animal. A line 16 is tied or secured to the eye-ring 12 and passed through a single bullet block pulley 18 to and through a surface mounted bullet lead block pulley 20 which is secured to the ceiling 14 adjacent ring 12. The free end of line 16 is then passed through to a second surface mounted bullet lead block pulley 22 which is secured to the ceiling 14 adjacent a stall wall 26 and from there downward to a cleat 24 secured to the stall wall 26 at a convenient site. Preferably, a knot 28 is tied in the line 16 between pulley 22 and cleat 24 so that the downward travel of hanger 30 will be stopped by knot 28 engaging pulley 22 and thus preventing accidental harm to the animal, or an attendant servicing the system. A loop 32 is tied at the free end of line 16 and passed around the cleat 24 to suspend hanger 30 above the center of the stall.

A swivel 34 is removably attached to a lower end of the single bullet block pulley 18 (described below). The hanger 30 is removably attached to the swivel 34 (described below). The pulley 18 offers a mechanical advantage to the operator hoisting and lowering the hanger 30.

Figure 2:
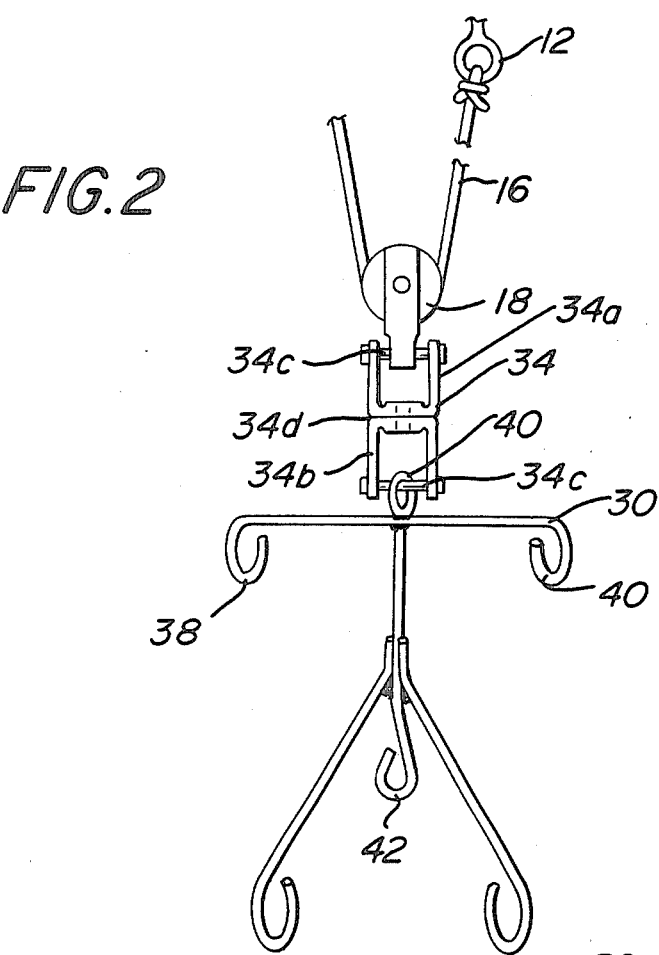
FIG. 2 is an enlarged elevational view of a portion of the apparatus which illustrates a hanger, a swivel and a portion of the system.

The single bullet block pulley 18, swivel 34 and hanger 30 are shown in greater detail in FIG. 2. Swivel 34 permits hanger 30 to universally rotate as the animal connected to a primary tubing system 50 (see FIG. 1) walks about the stall. The hanger 30 is constructed to support 5 or more fluid containers 36 from a plurality of hooks (e.g., 38, 40, 42). Each hook may support one or more containers. Two hooks 38 and 40 are purposely positioned above the remaining hooks, so that the containers on hooks 38 and 40 will empty first. This makes the addition of full containers easier and assists in maintaining a continuous flow of fluid from the containers. A center hook 42 is for suspending a container or containers of supplemental salt solutions, drugs, plasma, or blood for introduction into the primary tubing system 50. A ring 46 is affixed to the top of the hanger 30 to permit the removable attachment of the swivel 34 thereto. The swivel 34 is made of corrosion resistant materials and has a bearing 34d between the upper 34a and lower 34b swivel sections to reduce swivel binding created by the weight of the fluid containers and to insure the smooth universal rotation of the hanger 30. The swivel 34 also has removable cross-pins 34c to enable removable attachment of the swivel to pulley 18 and hanger 30. The hanger 30 is constructed as to keep the weight of fluid containers suspended therefrom as near to the center line of the hanger 30 as possible. This also helps to prevent any binding of swivel 34.

Figure 4:
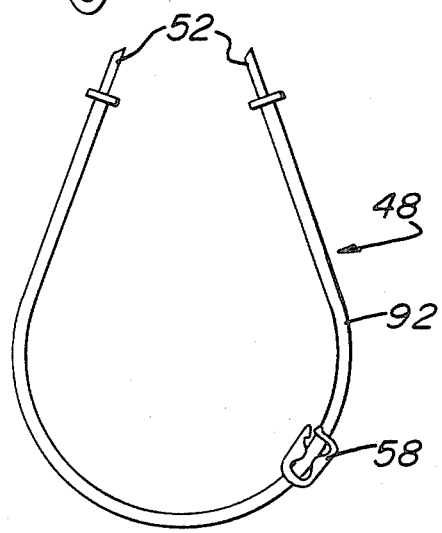
FIG. 4 is an enlarged elevational view of a secondary tubing system.
Figure 3:
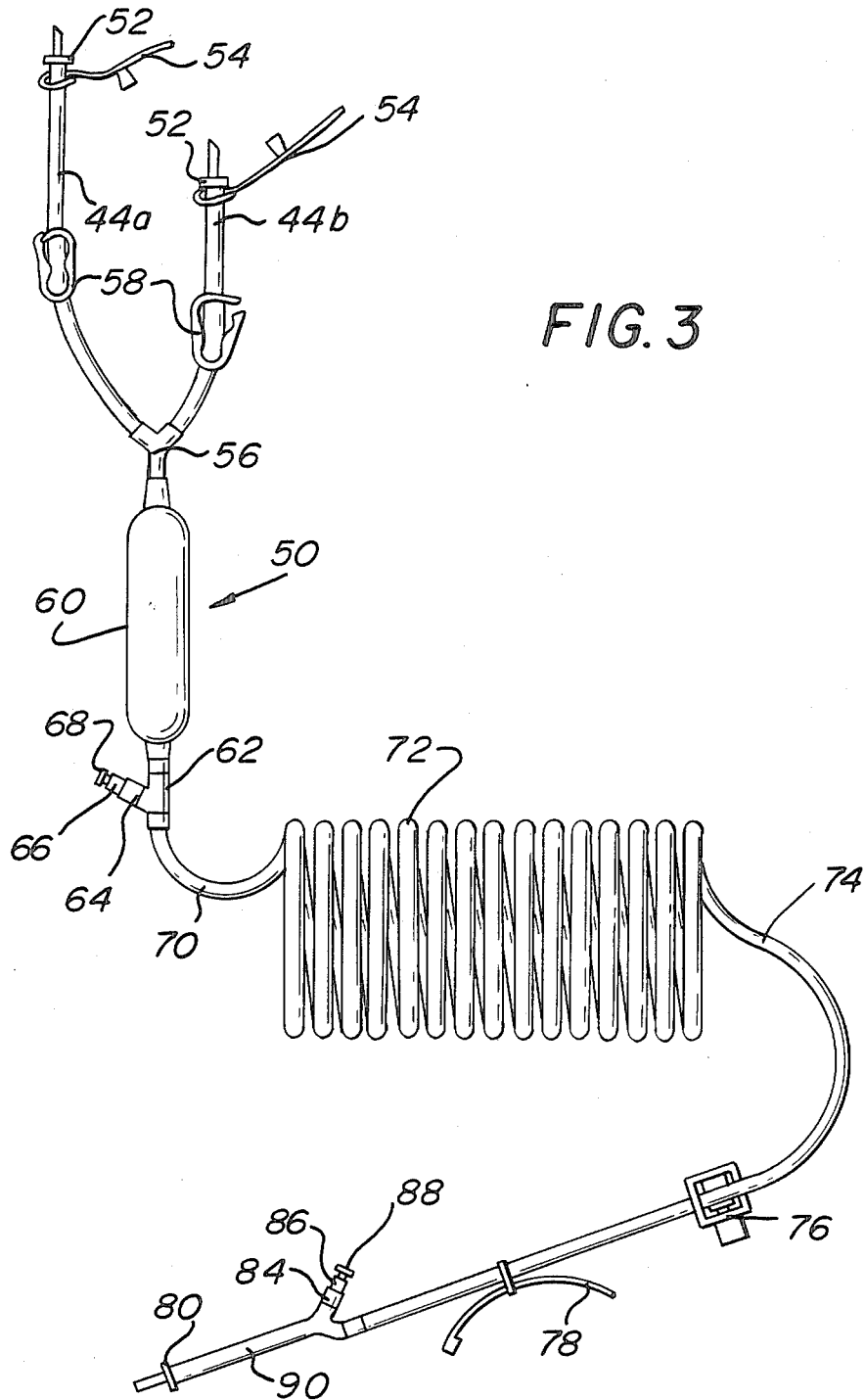
FIG. 3 elevational view of a primary tubing system.

A preferred embodiment of the primary tubing system 50 is shown in FIG. 3. Primary tubing system 50 conveys the fluids from the containers to the animal in a closed fashion. The secondary tubing 48, shown in FIG. 4, can be used to convey fluids from one container to another.

The primary system 50 has two connectors 52 at its uppermost end, the purpose of which are to enter the "universal" membrane-sealed ports in the bottom of the fluid containers. These fluid containers and the universal membrane-sealed ports are standard and well-known in the art. The connectors 52 are secured to tubing 44a and 44b which leads to the animal through a Y-connector 56. One length of tubing 44a is longer than the other 44b so that the primary tubing system 50 can be easily attached to fluid containers at a different or the same height on hanger 30. Ties 54, which secure the connectors 52 to the fluid containers 36, are adjacent the connectors 52 and tied or secured around tubing 44a and 44b. Ties 54 prevent the animal from inadvertently pulling the connectors 52 from the containers 36. A shut-off clamp 58 is placed about tubing 44a and 44b between connector 52 and Y-connector 56 to restrict or stop fluid flow in each arm of tubing.

A drip chamber 60 for limiting the introduction of air beyond this point and for serving as a means of monitoring the rate of fluid flow is connected to a base of the Y-connector 56. The construction of the drip chamber is well-known in the art. A second Y-connector 62, identical to the first is connected to the free or lower end of the drip chamber 60. A short length of tubing 64, followed by a fitting 66 and injection cap 68, is connected to the available side arm of Y-connector 62. The purpose of cap 68, fitting 66 and tubing 64 is to permit the introduction of plasma, drugs, and supplemental solutions into the primary tubing system 50 from the container(s) suspended from the center hook 42. A short length of tubing 70 followed by a coil 72 of resilient tubing is attached to the base of Y-connector 62. The coil 72 may have a diameter of about 7.0 cm and an overall (extended) length of about 3.66 meters. Of course these dimensions may be varied. A length of tubing 74 has an accurate flow control valve 76 fitted thereon. The flow control valve 76 is well-known in the art. The valve 76 is for controlling the overall rate of fluid flow to the animal. An adjustable moveable strap 78 for securing the primary tubing system to the animal's halter, mane, or neck is secured to tubing 74. The strap 78 can be secured to the animal's halter, mane or neck by any means such as tying, clamping, etc. (See FIG. 1) The strap 78 absorbs most of the tension force created by the coil 72 and the remainder of system 50 as the animal moves about, lies down or otherwise places a force on the system 50. Were it not for the strap 78, the entire force would have to be born by a catheter (or needle) connector 80 which connects the system 50 to the needle or catheter in the animal's vein. (See FIG. 1)

A Y-connector 82, identical to the others, is connected to the free end of tubing 74. A short length of tubing 84, followed by a fitting 86 and an injection cap 88, identical to injection cap 68, is connected to the side arm of Y-connector 82. A short length of tubing 90 is connected to the base of Y-connector 82. The standard catheter connector 80 is connected to the free end tubing 90. The catheter connector 80 is well known in the art and differs from the connector 52, in one aspect, by having a non-slanted end. A needle or catheter (not shown but well-known in the art) for insertion in the vein can be removably secured to connector 80.

The secondary tubing system 48 (FIG. 4) is composed of two connectors 52, preferably identical to those of the primary tubing system, and a length of tubing 92. Connectors 52 are attached to either end of tubing 92. A shut-off clamp 58, preferably identical to those on the primary tubing system 50 for stopping fluid flow, is attached to tubing 92 between connectors 52.

A schematic presentation of the intended use of the entire system is shown in FIG. 1. It is apparent from this drawing the large animal can move about the stall while receiving continuous fluid or drug treatment.

The present invention may be embodied in other specific forms without departing from the spirit or essential attributes thereof and, accordingly, reference should be made to the appended claims, rather than to the foregoing specification, as indicating the scope of the invention.

We claim:

1. An apparatus for the gravitational administration of fluids and drugs from containers to an animal comprising:
    means for hanging a plurality of containers;
    means for vertically moving and suspending the hanger means;
    means for swivelling the hanger means, the swivel means being connected between the hanger means and the vertically moving and suspending means;
    means for removably connecting at least one container of the plurality of containers to the animal, the removably connecting means being operatively associated with the plurality of containers;
    means for securing the connecting means to the animal, the securing means being adjustably and moveably secured to the connecting means; and
    means for tying the connecting means to the one container of the plurality of containers.

2. The apparatus according to claim 1 wherein the hanger means includes a hanger having a plurality of hooks, at least two hooks having a higher elevation than the remaining hooks, and a ring by which the swivel means is removably connected to the hanger.

3. The apparatus according to claim 1 wherein the vertically moving and suspending means further comprises:
    a ring adapted for securement to a ceiling;
    a pulley being removably connected to the swivel means;
    at least one surface mounted pulley being adapted for securement to the ceiling;
    a cleat adapted for securement to a wall; and
    a line being secured to the ring, passing through the pulley and the surface mounted pulley, and being securable on the cleat.

4. The apparatus according to claim 1 wherein the connecting means further comprises:
    at least two connectors, each connector adapted for receipt in a container;
    a length of first tube being secured to each connector, one first tube being longer than the other first tube;
    a first Y-connector, the tube being secured to each arm of the first Y-connector;
    a drip chamber being secured to a base of the first Y-connector;
    a second Y-connector, one arm of the second Y-connector being secured to an end of the drip chamber opposite the first Y-connector, the other arm being provided with an injection cap;
    a coiled tube being connected to the base of the second Y-connector;
    a second tube being connected to the free end of the coiled tube, and having a flow control valve;
    a third Y-connector, one arm being connected to the free end of the second tube, the other arm being provided with an injection cap;
    a third tube being connected to the base of the third Y-connector; and
    a connector being secured to the free end of the third tube.

5. The apparatus according to claim 1 comprising:
    means for interconnecting at least two of the containers.

6. The apparatus according to claim 5 further comprising a shut-off clamp.

7. A tubing system for the gravitational administration of fluids and drugs from containers to an animal comprising:
    at least two connectors, each connector adapted for receipt in a container;
    a length of first tube being secured to each connector, one tube for each connector and being longer than the other tube;
    a first Y-connector, the first tube being secured to each arm of the first Y-connector;
    a drip chamber being secured to the base of the first Y-connector;
    a second Y-connector, one arm of the second Y-connector being secured to an end of the drip chamber opposite the first Y-connector, the other arm being provided with an injection cap;
    a coiled tube being connected to the base of the second Y-connector;
    a second tube being connected to the free end of the coiled tube, and having a flow control valve and a securement strap placed thereon;
    a third Y-connector, one arm being connected to the free end of the second tube, the other arm being provided with an injection cap;
    a third tube being connected to the base of the third Y-connector; and
    a friction lock connector being secured to the free end of the third tube.

8. A device for use with apparatus for the gravitational administration fluids and drugs from containers to an animal comprising:
    a hanger having three or more hooks and the hooks being adapted for holding more than one container;
    at least two hooks having a higher elevation than the remaining hooks; and
    attachment means for securing the hanger to the apparatus for gravitational administration of fluids and drugs.

* * * * *

UNITED STATES PATENT AND TRADEMARK OFFICE
CERTIFICATE OF CORRECTION

PATENT NO. : 4,699,613
DATED : October 13, 1987
INVENTOR(S) : William J. Donawick and Betty L. Teichman It is certified that error appears in the above—identified patent and that said Letters Patent is hereby corrected as shown below:

Claim 1, line 2, between "from" and "containers" add -- a plurality of --; and line 4, change "a" to -- the --.

Claim 7, line 6, between "tube" and "being" add -- for each connector and --.

Claim 8, line 4, change "three or more" to -- a central axis, and at least four --, and change "and the hooks" to --, each hook --; line 5, change "more than one" to -- a --, and after "container" add -- each hook being turned inwardly toward said axis --; line 6, delete "at least", and after "the" add -- two --; line 7, between "hooks" and ";" add -- and laying in a plane through said central axis, the two remaining hooks laying in a second plane through said central axis, said first plane being substantially perpendicular to said second plane --.

Signed and Sealed this

Fifteenth Day of March, 1988

Attest:

DONALD J. QUIGG

Attesting Officer

Commissioner of Patents and Trademarks